United States Patent [19]

Gehrer et al.

[11] Patent Number: 5,118,883
[45] Date of Patent: Jun. 2, 1992

[54] PREPARATION OF GLYCOLS FROM FORMALDEHYDE

[75] Inventors: Eugen Gehrer, Ludwigshafen; Wolfgang Harder, Weinheim, both of Fed. Rep. of Germany

[73] Assignee: BASF Aktiengesellschaft, Ludwigshafen, Fed. Rep. of Germany

[21] Appl. No.: 728,166

[22] Filed: Jul. 10, 1991

[30] Foreign Application Priority Data

Jul. 21, 1990 [DE] Fed. Rep. of Germany ....... 4023255

[51] Int. Cl.$^5$ .................. C07C 31/20; C07C 29/141; C07C 29/145; C07C 29/132
[52] U.S. Cl. ..................................... 569/863; 568/864
[58] Field of Search ......................................... 568/863

[56] References Cited

U.S. PATENT DOCUMENTS

| 2,749,371 | 6/1956 | Kasehagan | 260/635 |
|---|---|---|---|
| 2,775,621 | 12/1956 | MacLean et al. | 568/863 |
| 2,868,847 | 1/1959 | Boyers et al. | 260/635 |
| 2,983,734 | 5/1961 | Sargent | 260/347.8 |
| 3,030,429 | 4/1962 | Conradin et al. | 568/863 |
| 3,055,840 | 9/1962 | Koch | 252/443 |
| 3,538,019 | 11/1970 | Capik et al. | 252/437 |
| 3,935,284 | 1/1976 | Kruse | 568/863 |
| 3,963,788 | 6/1976 | Kruse et al. | 260/635 C |
| 3,963,789 | 6/1976 | Kruse et al. | 260/635 C |
| 4,024,193 | 5/1977 | Kruse | 568/863 |
| 4,156,636 | 5/1979 | Muller et al. | 568/863 |
| 4,219,508 | 8/1980 | Wagner | 508/863 |
| 4,247,653 | 1/1981 | Wagner | 568/863 |
| 4,258,222 | 3/1981 | Mohring et al. | 568/863 |
| 4,270,992 | 6/1981 | Saito | 204/59 R |
| 4,300,003 | 11/1981 | Mohring et al. | 568/863 |
| 4,337,371 | 6/1982 | Kollar | 568/852 |
| 4,393,252 | 7/1983 | Kollar | 568/852 |
| 4,400,560 | 8/1983 | Richter et al. | 568/863 |
| 4,412,084 | 10/1983 | Kollar | 568/852 |
| 4,412,085 | 10/1983 | Kollar | 568/852 |
| 4,430,253 | 2/1984 | Dubeck et al | 502/185 |
| 4,496,781 | 1/1985 | Jacobson et al. | 568/862 |
| 4,565,896 | 1/1986 | Knifton et al. | 568/852 |
| 4,571,289 | 2/1986 | Griggs | 204/157.9 |
| 4,608,446 | 8/1986 | Mohring et al. | 568/863 |

FOREIGN PATENT DOCUMENTS

| 0071458 | 10/1984 | European Pat. Off. . |
|---|---|---|
| 0071457 | 6/1985 | European Pat. Off. . |
| 0147983 | 7/1985 | European Pat. Off. . |
| 0175558 | 9/1985 | European Pat. Off. . |
| 3018844 | 12/1980 | Fed. Rep. of Germany . |
| 3134046 | 11/1989 | Fed. Rep. of Germany . |
| 8612204 | 3/1988 | France . |

OTHER PUBLICATIONS

Lange, "Handbook of Chemistry" 10th ed. (1966) pp. 234 and 235.
J. Amer. Chem. Soc. 54, 4116 (1932).
J. Pr. Chem. 33, 321 (1886).
J61053235-A.
Chem. Ber. 84, 229 (1951).
Ann. 120, 295 (1861).
Z. Naturforsch. 38b, 1257 (1983).
J. Catal. 48, 354 (1977).
J. Agr. Chem. Soc. Jap. 44, 324 (1970).
Bull. Chem. Soc. Jap. 50, 1527 (1977).

Primary Examiner—J. E. Evans
Attorney, Agent, or Firm—John H. Shurtleff

[57] ABSTRACT

A process is described for the preparation of propylene glycol and ethylene glycol from formaldehyde, the first step involving conversion of the formaldehyde into a mixture of polyhydroxyl compounds in a conventional manner in an alkaline medium by self-condensation and the second step involving catalytic hydrogenolysis of this mixture with a hydrogen consumption of at least 0.5 mol of hydrogen per mol of formaldehyde employed for forming the polyhydroxyl compounds.

7 Claims, No Drawings

PREPARATION OF GLYCOLS FROM FORMALDEHYDE

The present invention relates to a process for the two-step preparation of glycols, in particular propylene glycol, from formaldehyde, the first step involving condensation of the formaldehyde to give polyhydroxyl compounds ("formose"), and the second step involving catalytic hydrogenolysis of the formose.

Propylene glycol is prepared in industry virtually exclusively by hydrolysis of propylene oxide. However, the synthesis of propylene oxide is complex or, in the case of the chlorohydrin synthesis, involves problems in disposing of toxic by-products.

There has therefore been no lack of attempts to obtain a propylene glycol from other starting materials.

Thus, numerous publications (e.g. J.A.C.S. 54 (1932), 4116–4117, U.S. Pat. No. 2,983,734, 2,749,371, 3,538,019, 2,868,847, FR 2,603,276, U.S. Pat. No. 3,055,840, 3,963,788, 3,963,789 or U.S. Pat. No. 4,430,253) have studied the hydrogenolysis of sugars to give mixtures of ethylene glycol, propylene glycol and glycerol, but this reaction has not come to industrial fruition.

Furthermore, the possibility of direct preparation of propylene glycol from formaldehyde has been described. Thus, for example, U.S. Pat. No. 4,496,781, 4,565,896 and JP 61/053,235 describe the hydroformylation (reaction with $CO/H_2$) and hydrogenation under superatmospheric pressure of mixtures of polyhydroxyl compounds which also contain glycols in low space-time yields.

Furthermore, DE 31 34 046, EP 71 458, EP 71 457, EP 147 983 and U.S. Pat. No. 4,412,085 disclose the free-radical addition of methanol to formaldehyde to give ethylene glycol. However, this process is uneconomic due to the large amount of expensive free-radical initiators required. JP 59/220,638 discloses that the photochemical route involving irradiation of aqueous formaldehyde solutions gives small amounts of ethylene glycol and propylene glycol. Finally, the electrochemical coupling of formaldehyde as in DE 30 18 844 gives small amounts of propylene glycol in addition to ethylene glycol. All these processes have hitherto given only unsatisfactory yields of glycols, and the reaction products contained only very small amounts of the propylene glycol desired.

It is therefore an object of the present invention to prepare propylene glycol in a simple manner from readily accessible starting materials.

We have found that this object is achieved by a process for the preparation of propylene glycol and ethylene glycol from formaldehyde, the first step involving conversion of formaldehyde into a mixture of polyhydroxyl compounds in a conventional manner in an alkaline medium by self-condensation, and the second step involving catalytic hydrogenolysis of this mixture with a hydrogen consumption of at least 0.5 mol of hydrogen per mol of formaldehyde employed for forming the polyhydroxyl compounds.

The smoothness of this method was surprising since the formose mixture obtainable by self-condensation of formaldehyde contains more than 40 principal compounds, including, for example, non-natural, branched polyhydroxyl compounds in addition to glucose, fructose and xylose. This means that the wide range of compounds produced in the formose reaction is recombined to give a few valuable products, and formaldehyde can be converted into propylene glycol and ethylene glycol in high yield by a two-step reaction.

The formose reaction was disclosed a considerable time ago in Ann. 120 (1861), 295 and J. Pr. Chem. 33 (1886), 321, and in more recent literature in Pfeil Chem. Ber. 84 (1951), 229, G. Harsch, Z. Naturforsch. 38b 1983), 1257–1268, but has not yet been developed commercially.

In detail, the following procedure is expediently used for the process according to the invention:

a) Formose reaction

The formose solution can be prepared by a number of methods, as described, for example, in Alvin Weiss, J. Catal. 48 (1977), 354–364, T. Mizuno, J. Agr. Chem. Soc. Jap. 44, No. 7 (1970) 324–331, and Y. Shigemasa Bull. Chem. Soc. Jap. 50 (6) (1977), 1527–31, to which we refer.

In general, basic catalysts, such as CaO, SrO, BaO, TlOH or PbO, organic bases, or thiazolium or imidazolium salts are used. The formose reaction can be carried out continuously, batchwise or semicontinuously. The formaldehyde can be introduced in solution, in gas form or in the form of paraformaldehyde or trioxane. The reaction temperature is from room temperature to 110° C., and the pH is from 5 to 12, depending on the catalyst system.

b) Catalytic hydrogenolysis

The crude formose mixture produced is expediently fed directly to the hydrogenolysis step. In many cases, however, it is advantageous to first separate off the catalyst employed for the self-condensation of the formaldehyde. In the case of the hydroxides of Ca, Sr, Ba or Pb, the catalyst can easily be removed, for example by precipitation using $H_2SO_4$.

According to a preferred embodiment, the hydrogenolysis is preceded by reduction under mild and neutral or acidic conditions of the carbonyl groups or acetal groups in the compounds present in the formose, in order to reduce the extent of side reactions, such as resin formation, and the formation of lactic acid or sugar acids which are difficult to reduce. This reduced formose is referred to below as formitol.

In principle, any hydrogenation catalyst used for carbonyl compounds is suitable for this hydrogenation. This reaction is particularly preferably carried out using an Ru or Ni catalyst at from 100° to 150° C. and from 20° to 200 bar of $H_2$.

In order to achieve highly selective formation of ethylene glycol and propylene glycol in the hydrogenolysis, which may, if desired, be carried out after previous hydrogenation, of the complex formose mixture comprising more than 40 different straight-chain and branched polyhydroxyl compounds, it is necessary for this mixture to take up, during all the reactions with hydrogen, i.e. during the hydrogenation and hydrogenolysis, at least 0.5 mol of hydrogen per mol of formaldehyde employed for producing the formose mixture. The take-up of hydrogen by the formose mixture can easily be monitored and controlled using conventional pressure measurement and control valves under the reaction conditions given below.

The hydrogenolysis of the formose mixture or of the formitol mixture is carried out at from 50° to 300° C., in particular at from 100° to 250° C., preferably at 180° to 220° C., and at a hydrogen pressure of from 1 to 1000 bar, preferably from 10 to 600 bar, in particular from 40 to 100 bar, using a homogeneous or heterogeneous hydrogenation catalyst. Preference is given to a Cu-, Ni- or Ru-containing catalyst on a carrier or as a suspension (Raney nickel). At low temperatures, it is also possible to use a homogeneous catalyst, such as $Ru(PAr_3)_4$.

The catalytic hydrogenolysis reaction mixture is worked up by conventional separation methods. It is expedient to first separate off the water and subsequently to subject the glycol mixture to precision distillation. The lactic acid formed in the reaction as a by-product can be hydrogenated by conventional methods (as described, for example, in EP 175 558) to give a further fraction of propylene glycol.

EXAMPLE a) Formose preparation

Initial phase of the reaction 40 g of fructose and 60 g of water are introduced into a 100 ml flask equipped with reflux condenser, pH electrode, thermometer, and inlets for formaldehyde solution and $CaO/H_2O$, and the mixture is warmed to 90° C. 4 g/min of the 5% strength suspension of CaO in water are then metered until a pH of 9.8 has become established during which the solution becomes yellow-brown. The addition of 5 g/min of 37% strength formaldehyde is then commenced. When the reaction has started (the reaction is exothermic and the reaction mixture may start to boil), the temperature is slowly reduced to 60° C.

Steady state

At 60° C., 5 g/min of 37% strength formaldehyde solution and 4 g/min of CaO (5%) are metered in. A pH of from 8 to 10 is established. The solution is pale yellow. After leaving the reactor, it still contains a little residual formaldehyde, which reacts completely on storage at room temperature. This steady state is very stable.

Work-up

For the subsequent hydrogenation, the calcium is precipitated using sulfuric acid, and a pH of 3 is established. Each liter of formose requires about 196 ml of 20% strength sulfuric acid. The system is buffered at a pH of about 3.5, and the calcium sulfate does not precipitate until about ¾ of the necessary amount of sulfuric acid has been added.

Analysis:

Evaporation of the salt-free, acidic formose at 60° C. under reduced pressure gives from 100 to 105% of an organic residue containing about 6% of permanently bound water. The yield of organic products is thus about 97%. The product is a pale yellow, viscous, tacky material which is no longer capable of flowing. The residual formaldehyde content (including the acetal-bound formaldehyde) is determined as 0.001% using dinitrophenylhydrazine derivatives. GC analysis of the trimethylsilyl derivatives indicates a mixture of polyhydroxyl compounds, preferably having from 4 to 7 carbon atoms in the molecule.

b) Hydrogenation of the formose mixture to give formitol 60 ml of the acidic, salt-free formose prepared as in a), but not evaporated, and 30 g of catalyst (5% Ru on carbon) are hydrogenated at 120° C. for 30 minutes with stirring in a 300 ml autoclave at a hydrogen pressure of 90 bar. The reaction commences even during the heating phase (hydrogen consumption). Even after the same catalyst has been re-used several times, an aqueous polyol solution (formitol) which is virtually free from carbonyl and acetal groups is obtained.

c) Hydrogenolysis 60 ml of the formitol solution prepared as in b), 3 g of CaO and 30 g (dry weight) of catalyst (5% Ru on carbon, poisoned with $Na_2S$ 1:1, in order to suppress the methanization reaction) are subjected to hydrogenolysis for 2 hours at 200° C. with stirring in a 300 ml autoclave at a hydrogen pressure of 90 bar. The filtrate contains (determined by GC analysis of the trimethylsilyl derivatives), based on the formaldehyde employed, after the same catalyst has been re-used several times (6 to 8 times):

| mol % |
|---|
| 44.4 of propylene glycol |
| 23.3 of ethylene glycol |
| 8.3 of 1,2-butylene glycol |
| 9.5 of 2,3-butylene glycol |
| 10.3 of lactic acid |
| 95.9 sum of the valuable products |

During the hydrogenation of the formose solution to the formitol solution and subsequent hydrogenolysis thereof, a total of 0.54 mol of hydrogen was consumed per mol of formaldehyde employed for preparing the formose.

We claim:

1. A process for the preparation of propylene glycol and ethylene glycol from formaldehyde, which comprises, in a first step, converting formaldehyde into a mixture of polyhydroxyl compounds in a conventional manner in an alkaline medium by self-condensation, and, in a second step, subjecting this mixture to catalytic hydrogenolysis with a hydrogen consumption of at least 0.5 mol of hydrogen per mol of formaldehyde employed for forming the polyhydroxyl compounds.

2. A process as claimed in claim 1, wherein the carbonyl and acetal groups of compounds of the polyhydroxyl compound mixture are subjected to catalytic hydrogenation before the catalytic hydrogenolysis.

3. A process as claimed in claim 1, wherein the catalytic hydrogenolysis is effected by heterogeneous catalytic hydrogenation at from +50° to 300° C. and a hydrogen pressure of from 10 to 600 bar.

4. A process as claimed in claim 3, wherein the catalytic hydrogenolysis is carried out using calcium oxide.

5. A process as claimed in claim 1, wherein the self-condensation of the formaldehyde is carried out at a pH of from 8 to 10 using calcium hydroxide as catalyst.

6. A process as claimed in claim 2, wherein the hydrogenation is carried out at from 20° to 180° C. and a hydrogen pressure of from 1 to 600 bar on a ruthenium or nickel catalyst.

7. A process as claimed in claim 1, wherein propylene glycol and ethylene glycol are isolated from the reaction mixture by distillation or extractive distillation.

* * * * *